(12) United States Patent
Doyle

(10) Patent No.: US 6,552,338 B1
(45) Date of Patent: Apr. 22, 2003

(54) ION PHOTON EMISSION MICROSCOPE

(75) Inventor: Barney L. Doyle, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 98 days.

(21) Appl. No.: 09/882,400

(22) Filed: Jun. 14, 2001

(51) Int. Cl.$^7$ .............................. G01N 23/00; G21K 7/00
(52) U.S. Cl. ........................ 250/309; 250/306; 250/308; 250/310; 356/73; 356/300; 356/326; 356/328; 356/337.1
(58) Field of Search ................................. 250/306, 308, 250/309, 310; 356/73, 300, 326, 328, 237.1

(56) References Cited

U.S. PATENT DOCUMENTS

| | | | | |
|---|---|---|---|---|
| 6,043,882 A | * | 3/2000 | De Wolf et al. ............ 356/326 |
| 6,088,097 A | | 7/2000 | Uhl ............................. 356/318 |
| 6,108,082 A | * | 8/2000 | Pettipiece et al. .......... 356/301 |
| 6,291,823 B1 | * | 9/2001 | Doyle et al. ................ 250/308 |

OTHER PUBLICATIONS

Doyle, B.L., Vizkelethy, G., Walsh, D.S., Senftinger, B. and Mellon, M., "A new approach to nuclear microscopy: the ion–electron emission microscope," Nucl. Instr. and Methods in Phys. Res. B, 1999, 158, 6–17.

Doyle, B.L., Walsh, D.S., Renfrow, S.N., Vizkelethy, G., Schenkel, T. and Hamza, A.V., "Nuclear Emission Microscopies," presented at the $7^{th}$ Intl. Conf. on Nuclear Microprobe Tech. & Appl., Sep. 10–15, 2000.

Firmani, C., Ruiz, E., Carlson, C., Lampton, M., Paresce, F., "High–resolution imaging wtih a two–dimensional resitive anode photon counter," Rev. Sci. Instrum., 1982, 53, 5, 570–574.

\* cited by examiner

Primary Examiner—John R. Lee
Assistant Examiner—Erin-Michael Gill
(74) Attorney, Agent, or Firm—Elmer A. Klavetter, Agent

(57) ABSTRACT

An ion beam analysis system that creates microscopic multidimensional image maps of the effects of high energy ions from an unfocussed source upon a sample by correlating the exact entry point of an ion into a sample by projection imaging of the ion-induced photons emitted at that point with a signal from a detector that measures the interaction of that ion within the sample. The emitted photons are collected in the lens system of a conventional optical microscope, and projected on the image plane of a high resolution single photon position sensitive detector. Position signals from this photon detector are then correlated in time with electrical effects, including the malfunction of digital circuits, detected within the sample that were caused by the individual ion that created these photons initially.

30 Claims, 2 Drawing Sheets

ION PHOTON EMISSION MICROSCOPE

This invention was made with Government support under Contract No. DE-AC04-94AL85000 awarded by the Department of Energy. The Government has certain rights in the invention.

BACKGROUND OF THE INVENTION

This invention relates to a system for applying the effects of high-energy ion radiation upon materials, semiconductors, insulators and the resultant function or malfunction of electronic or optical circuits and discrete devices and, more particularly, to a system for correlating the impact point of an ion measured by projection imaging of ion-induced photons with the effect of that ion upon the sample itself.

The signal produced by the emission of photons from a sample bombarded by high energy (MeV) ions has been used for many years on conventional nuclear microprobes, and on almost all accelerators, for viewing the beam during focussing and other beam adjustments such as steering and scanning. For these purposes the photons are not imaged. They are merely observed visually through high power microscopes or with charge-coupled device (CCD) cameras.

A physics application has emerged from this science, which is called Ionolumenescence which has been extensively applied in the field of Geology. In Ionolumenescence, a beam of ions is focused and then scanned across a sample specimen while measuring the intensity or in some cases the actual energy spectrum of emitted photons. Other applications have arisen in fields such as biology, where luminescent microscopes have been developed for studying biological objects (U.S. Pat. No. 6,088,097, issued on Jul. 11, 2000).

Nuclear microprobe analysis is currently performed by focusing MeV ions onto a sample and then scanning the ion beam in a flying spot analysis. The nuclear, atomic, or charge collection signals that are created by the interaction of the ions with the sample constitute the detected signal. The location from which the signal originates on the sample is known by the position of the scanning ion beam at the time the signal is created and detected. The position of the "flying spot" is derived from the scanning apparatus that moves the focussed ion beam spot back and forth across the sample. This standard nuclear microscopy is not always applicable in certain accelerator laboratories due to the difficulty in focussing ions with high magnetic rigidity and/or poor beam chromaticity for cyclotrons, linacs and older Van de Graaff style electrostatic ion accelerators. There can also be problems in clearly forming the object image for standard microbeam systems when the depth of penetration in slit materials (for very high ion energies) becomes comparable to the object slit diameter. High-energy accelerator labs can also have higher levels of radiation in the target areas, making hands-on real-time adjustments of the microbeam system and direct viewing of the beam spot on fluorescing materials impossible. This seriously complicates the procedures used in most microbeam applications to obtain an optimal beam focus.

Alternatives to traditional nuclear microprobe analysis emerged with the invention of Ion-Electron Emission Microscopy (IEEM) (Doyle, B. L., Walsh, D. S., Vizkelethy, G., Senftinger, B, Mellon, M., 1999, Nucl. Insts. and Meth. in Phys. Res, B, 158, 6). With Nuclear Emission Microscopy, the ion beam is only partially focused so as to fill the field of view of a special emission particle microscope system fitted with a single particle Position Sensitive Detector (PSD). When a single ion strikes the sample, the emitted secondaries (e.g. electrons, photons, ions) are projected at great magnification onto this PSD where position signals are generated. These X and Y signals are then put into coincidence with other signal made by this same ion in a fashion completely analogous to traditional nuclear microprobe analysis. These Nuclear Emission Microscopes techniques currently includes IEEM and Highly Charged Ion-Secondary Ion Mass Spectroscopy (HCI-SIMS) (Doyle, B. L., Walsh, D. S., Renfrow, S. N., Vizkelethy, G., Schenkel, T., and Hamza, A. V., 7$^{th}$ Intl. Conf. on Nuclear Microprobe Tech. & Appl., 2000; incorporated herein by reference). These techniques utilize accelerators to provide the ion beam.

A microbeam apparatus would be useful that does not require an accelerator and that can obtain simultaneous information on the characteristic of a sample when impinged by an ion as well as the position of the ion strike.

DETAILED DESCRIPTION OF THE INVENTION

Figure 1:
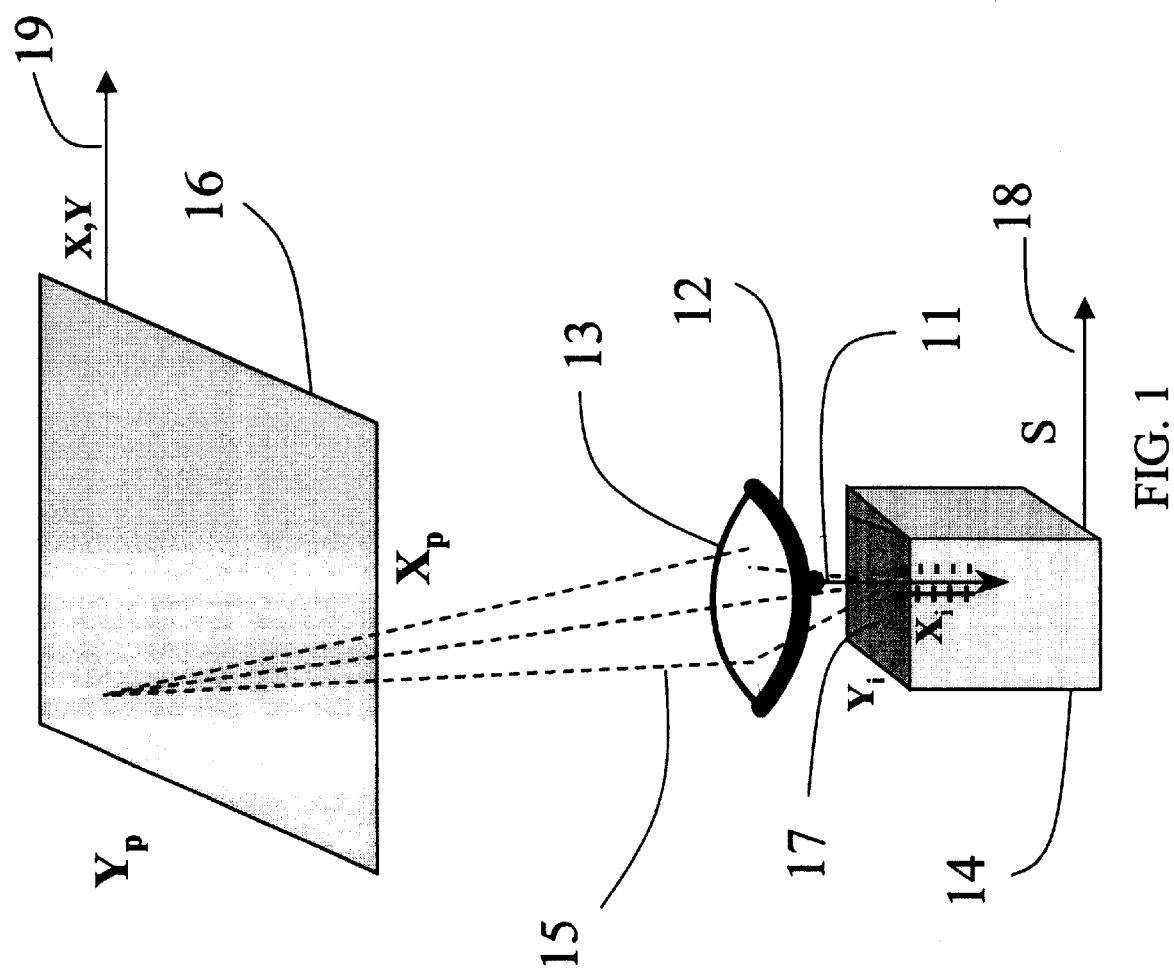
FIG. 1 is an illustration of the various elements of the Ion Photon Emission Microscope.

The Ion-Photon Emission Microscope (IPEM) apparatus of the present invention allows performing nuclear microscopy with a simple system that does not require an accelerator. The apparatus of the present invention discards the need for the precisely focussed and scanned ion beams of the prior art in favor of utilizing an unfocussed ion source. Instead of relying upon knowledge of where the ion beam spot is via the scanning system at the time a radiation effect is detected, this invention precisely images the position of photons emitted from the surface from a signal resulting from an interaction of an ion with the surface of a sample, or a phosphor coating applied to the sample surface. This imaging is done with much of the hardware already employed with single photon emission microscopes, using an optical microscope to project the image of ion induced photons at high magnification onto a very sensitive single photon X-Y position detector to map the location of the point of emission of the collected photons from the sample surface. Using coincidence techniques, generation and detection of these emissions of these photons at the mapped positions on the sample surface is correlated with the ion-induced signals from the device or material sample under test to match a particular ion interaction to a particular place on the sample.

The apparatus of the present invention improves various Radiation Effects Microscopies such as Ion Beam Induced Charge Collection (IBICC), Time Resolved-IBICC (TRIBBIC), and Single Event Effects (SEE) Imaging to allow 2-D images at high resolution to be obtained without an accelerator. IPEM offers numerous advantages to traditional flying-spot nuclear microprobe analysis, and almost all of these advantages stem from the fact that photons are much easier to focus/project than the MeV ions used for scanning in the prior art systems. IPEM is also particularly attractive for applications on cyclotrons or linacs, which have traditionally been all but excluded from nuclear microanalysis because of poor beam quality.

The IPEM has other applications in radiation effects microscopy including time resolved IBICC and analysis of Single Event Effects (SEEs) in integrated circuits. Density variations in samples can also be measured using IPEM in combination with ion-energy loss spectrometries. Crystalline orientation and quality could be microscopically examined by combining IPEM with transmission channeling contrast microscopy. The IPEM technique will be most effective for ion beam analyses with a extremely high event probability so that single ions can be used. The high energy ions to be used with IPEM can be virtually any element or isotope from protons to plutonium. High energy in this context is meant to include ion energy levels at or above about 1 MeV.

Data have demonstrated the potential for lateral resolution to be in the 1–2 micron range. The replacement of the very complex ion beam focussing/scanning systems in prior art machines with the projection imaging of the emitted photons with readily available optics significantly reduces the costs involved in making the types of measurements done by this class of systems. Also, because this invention avoids ion focusing, certain ion microbeam analyses previously limited to applications involving complex, large and expensive particle accelerators can be performed using simple, small and inexpensive radioactive alpha particle or even fission sources, and be performed in room air with a specially modified optical microscope.

In the Ion Photon Emission Microscope (IPEM) apparatus of the present invention, the production rate and energy of the detected photons is unimportant in so far as what is actually being measured by the ions about the sample. The IPEM apparatus results in two signals where one is used for indirect measurement of the precise position where each ion impinging on the sample actually strikes and one is used for measuring a characteristic of the sample. It is important for the determination of the precise position where each ion impinges that the sample, or a phosphor coating applied to the surface of the sample, have high ion-induced photon production efficiency, and that this first emission signal that is used for determining the position of the impinging ion be of an energy detectable with high probability by the single photon position sensitive detector (PSD). A second signal generated by a sensor means results from the sample itself after interaction with the impinging ion to give a characteristic property of the sample. Characteristic properties that can be determined include but are not limited to electrical properties such as electron/hole mobility, lifetime, charge collection efficiency, critical charge for single event effects and material properties such as density, crystal quality and crystal orientation. The correlation of these two signals thus provides both the characteristic property of the sample when impinged by the ion (where the characteristic property is determined by the nature of the analysis of the sample) as well as the precise location of the impinged ion.

The sample upon which the ions are impinged depends on the desired application. The sample could be a liquid, a specimen of biological or geological origin where property changes occur when impacted by a high energy ion, or could be an electronic or photonic component, such as a detector, transistor, diode, laser, semiconductor digital circuit, memory component, central processing unit or communications device. The sensor means associated with the sample depends on the sample and the application for the sample. The sensor means could determine the presence of a malfunction of a semiconductor digital circuit, providing a signal associated with the malfunction by the generation of a voltage pulse. The sensor means can also be an integrated circuit tester adapted for measurement of broad beam single event effects testing of static and dynamic random access memories and microprocessors. The sensor means can be used in some applications to measure transients occurring in the characteristic property as each ion strikes the sample surface and generally provides a signal pulse with the pulse height proportional to the characteristic property. The sensor means can also comprise a charge sensitive electronic preamplifier electronically connected to the sample, followed by a spectroscopic amplifier to produce a pulse whose height is proportional to the collected charge following the impact of an individual ion. The particular sensor means utilized results from a user's application.

An IPEM experiment is based on the well-known phenomenon that each ion strike to the sample can produce one or more photons from the near surface region of the target. These photons are then used to determine the position of the ion strike using the optical lens system to project these photons onto a high resolution X-Y position sensitive single photon detector (PSD).

An illustration of the ion beam—target—microscope—PSD system interactions is shown in FIG. 1. An ion beam 11 from a radioactive particle source (such as an alpha particle source) 12 on a lens or optic system 13, is exposed to a sample 14. Iono-luminescent photons 15 produced on the sample 14 are imaged by projection using a optic system 13 (such as a lens or microscope) and single photon position sensitive detector (PSD) 16. These photons are used to determine the X-Y position of each ion strike on the sample. The signals (S) 18 from the sample, such as from ion beam induced charge collection (IBICC), Single Event Effects (SEE), Single Event Upsets (SEU), ion microbeam tomography, secondary ion mass spectroscopy, or any ion beam analysis involving single incident ions, are put into coincidence with the X-Y position signals 19 and correlated to form (X,Y,S) lists, where the coordinates are given by the X and Y values and event S is the sample characteristic value generally represented by some signal pulse height. These lists are then processed to make high resolution images showing the sample characteristics as a function of position. In the apparatus of the present invention, there is no need to focus the incident ion beam and no accelerator is required. Moreover, the apparatus does not require a special environment and can be used in ambient air. In one embodiment, a phosphor coating 17 on the surface of the sample 14 increases the ion-induced photon production efficiency.

Figure 2:
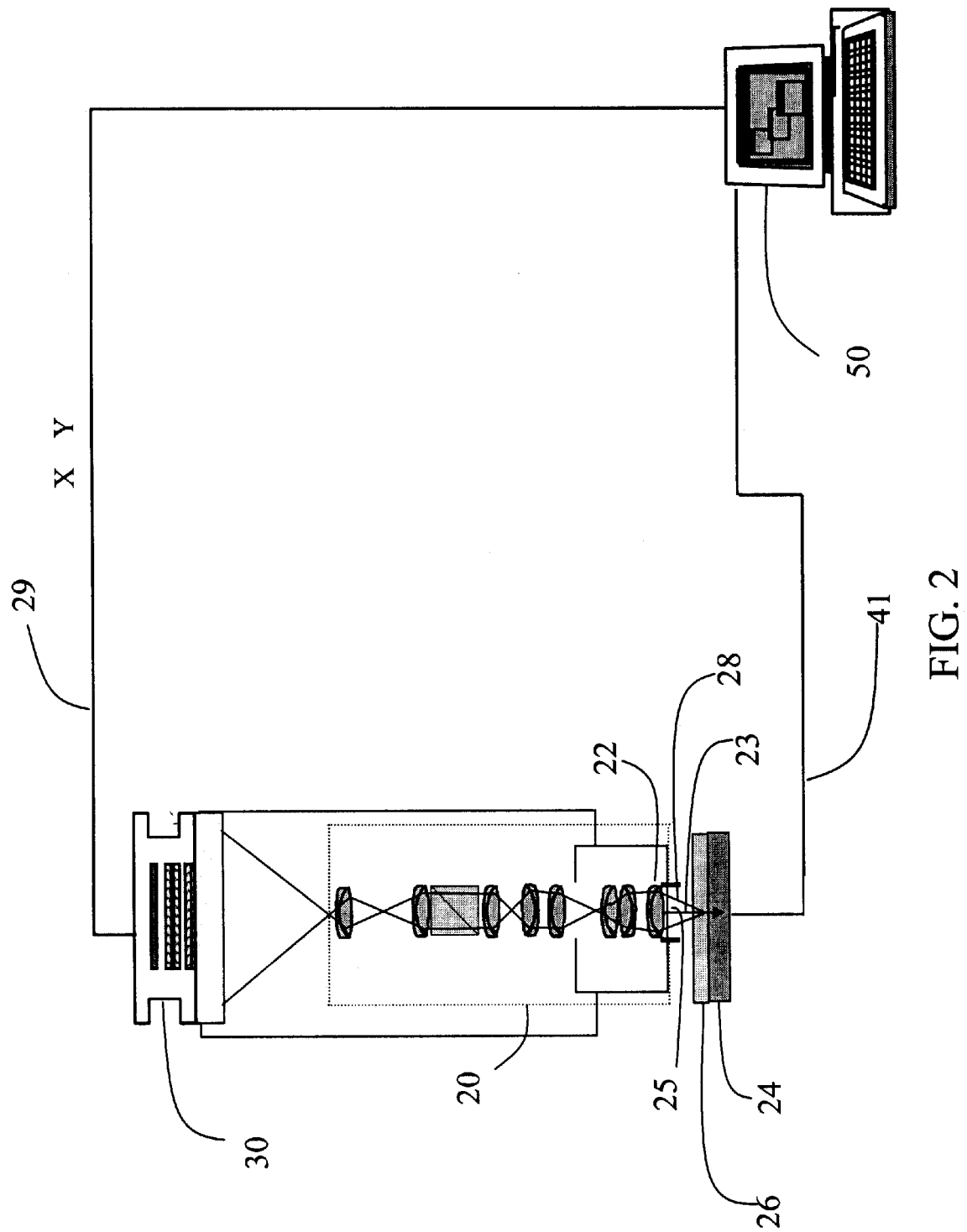
FIG. 2 is a drawing of the apparatus of the present invention.

A schematic of the IPEM is shown in FIG. 2, including the electronics and data acquisition system. Variations from and substitutions for the various individual components in this system will be apparent to those of skill in this art. A means to generate an ion beam is required. The means can be an accelerator as is standard in the art but can also be a radioactive alpha emitter source (such as the alpha emitter source 12 shown in FIG. 1) that can be coated on the objective lens 22 of the microscope lens system 20 as shown in FIG. 2 as well as a fission fragment source at or near the object lens of the microscope. The alpha particles (ion beam) 23 produced are directed at the surface of a sample 24 through an aperture 25. As shown in FIG. 2, the sample 24 has a phosphor coating 26 on the surface to increase the ion-induced photon production efficiency; some application will not require this phosphor coating to achieve adequate photon production efficiency. When the ion beam 23 impinges on the phosphor coating 26, generally at normal incidence, a first signal 28 (photons) is produced which is transmitted through the microscope lens system 20 to the single photon position sensitive detector 30. The position sensitive detector 30 transmits a signal 29 containing X-Y position information to electronic means 50. When the ion beam 23 impinges on the sample, a second signal 41 is produced from the sample that is also transmitted to electronic means 50 and that provides a measure S of some characteristic of the sample 24. The electronic means 50 contains a coincidence circuit that correlates the first signal X-Y position data from the ion beam impinging on the sample surface with the resulting second signal 41 representing the sample characteristic to give a (X,Y,S) datum point. Multiple ion strikes yields a list of (X,Y,S) points that can be used to build a tabular data file or, more commonly, a high resolution image of the sample characteristics S as a function of position.

In one embodiment, the microscope lens system 20 is a JOEL OM-40 microscope, where the beam 23 passes through holes in both a prism and objective lens. The photons collected by the OM-40 are made parallel by an objective lens located approximately 4 mm upstream of the sample, then is deflected at 90 degrees by the prism, transits outside the system to another prism, to finally, the eyepiece lens and a CCD camera. The eyepiece selected was of the lowest power to provide the maximum viewing area. The sample viewing field was up to 1 mm. Clearly, ion strikes that occur outside this field of view may produce ion beam signals from the target but no photon position signals. Therefore, in this and any other IPEM configuration, the purpose of the aperture 25 is to limit ion strikes on the sample to within the field of view of the photon detector. This is especially important for measurements that are sensitive to radiation damage, or other ion fluence effects.

The OM-40 can be used as an invacuo microscopic system for viewing the sample utilizing an accelerator as the ion source. This microscope has a magnification of 300–1000×, and because of the lens hole, can view the sample during ion irradiation, which is a requirement for IPEM. The accelerator can be replaced by a coating of a radioactive alpha emitter applied to the objective lens of the microscope or by a fission fragment source at or near the objective lens of the microscope. In this case, this lens would need no hole, since the ions are generated at or near the surface of this lens. This radioactive source embodiment would also not have to be placed in a vacuum system.

Effective photon generation and detection and position recording is critical to the IPEM technique. The system poses several requirements including the efficient generation of photons, efficient detection of photons, 2-D imaging capability, and sufficient time-resolution for the coincidence function. Photon generation can be maximized by coating a thin phosphor layer 26 onto the sample 24. Efficient detection of the photons is accomplished by employing optics 20 coupled to a commercial single photon position sensitive detector 30. A detailed description of a single photon PSD is given by Firmani et al. (Firmani, C., Ruiz, E., Carlson, C., Lampton, M. and Paresce, F., Rev. of Sci. Instr., 1982, 53, 5, 570–574).

The PSD generally consists of a transparent window, followed by a photoelectron converter, such as a bialkali thin film, and then a multi-stage microchannel plate (MCP) electron multiplier directly coupled to a charge-division position encoder (resistive anode encoder, RAE). The MCP configuration used ensures the high electron gain (approximately $2\times10^7$) required for high position resolution (100 μm FWHM across 40 mm diameter active area) while maintaining a tight gain pulse-height distribution for single electron initiated events. A PSD resolution of 100 μm at the high microscope gain of 300× corresponds to a resolution at the sample of only 0.3 μm. In operation, photons impact the photoelectron converter on the vacuum side of the transparent window and these electrons then travel to the MCP surface located just behind this converter. This results in an electron cascade that is multiplied by the MCP to a measurable level and the resulting charge cloud is electrostatically focused onto the surface of the RAE encoder in an X-Y location corresponding precisely to the location of the incident event on the input MCP. In a standard system, the charge diffusing in the RAE is divided among four collection terminals in a ratio proportional to position in the X and Y axes. The output is fed to a four-channel charge-sensitive amplifier/shaper module. The photon position sensitive detector can additionally comprise a charge coupled device as well as a CMOS image censor.

From the ratio of the preamplifier output signals, the readout electronics compute the X and Y coordinates of each event. These coordinates are output as analog pulses where amplitude is proportional to position. In addition, the position analyzer contains discriminators and pulse-pile-up circuits to veto events that are too low or high in gain, or arrive too close together, to be properly imaged. The X-Y analog outputs can then be connected to the external analogue to digital converters (ADCs) used in a multiparameter data acquisition system and to a conventional analog variable persistence X-Y oscilloscope to display real time single photon images. The system used has a relatively high instantaneous dynamic counting range extending from the low count rate of the MCP background (10 cps) up to 100,000 detected events/sec (with random arrival statistics, corresponding to 4 usec dead time per event).

The efficiency of the bialkali converter is approximately 20%, and the detection efficiency of the MCP is in the range of 50%. This should give the single photon PSD system a total efficiency in the 10% range. 100 psec FWHM time resolution for the PSD is obtained by an auxiliary MCP pickoff circuit which senses the time-of-passage of the single event through the MCP.

As part of the electronic means 50 in one embodiment, the detector X and Y outputs are digitized by ADCs and fed to two inputs of an 8 parameter MPA/PC multi-parameter system. This system operates in list mode, capturing data octets of up to 13 bits of X, 13 bits of Y and the desired number of digital bits from the energy parameters obtained from the separate detectors used for the IPEM signals 41 from the sample. These data octets are written to fixed disk memory in the PC as sequential data events and can be simultaneously histogrammed in RAM memory and displayed in real time. In addition, the multiparameter data system offers full time-coincidence capability between parameters, so events are accepted only if they fall into defined time ranges on each parameter. A list of events (X,Y,S) is produced which is exactly the type of list currently used in conventional ion-beam induced charge collection (IBICC) measurements of semiconductor circuits.

A number of samples were analyzed using the system of this invention. These samples included several phosphor coated PIN diodes. One phosphor utilized was Thiogallate, or $Sr_2GaO_5$:Eu(II). This phosphor was rough and consisted of 5 um particulates deposited by sedimentation. Thinner and more uniform phosphors could be realized using other materials (e.g., organic phosphors) and/or deposition techniques (e.g. evaporation or spin-on processes). Nevertheless, the Thalogallate is very bright and provided ideal samples for these tests. High resolution 2-D images were produced, showing, for example, ionolumenscence and IBICC images. The results from these samples demonstrate that the position of the ion impingement can be determined with a resolution in the 5–10 micron range, limited by the coarseness of these phosphor grains, and that these determined positions can be correlated to the characteristic sample property produced by the ion impingement with a high resolution 2-D image produced.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. An apparatus for correlating, from the interaction of a high energy ion with a sample, a position signal and a signal representing a sample characteristic property, comprising:

an unfocussed source of high energy ions directed at a surface of a sample;

said sample coated with a thin phosphor from which ion-induced photons are emitted in response to impacts from high energy ions;

a photon projection system to refocus and project individual ion-induced photons produced on the sample by said high energy ions, said photon projection system having an image plane;

a photon position sensitive detector placed at the image plane of the photon projection system, said detector producing a first signal by which the impact point (X,Y) of each ion is determined;

a sensor means associated with the sample to detect a characteristic property of the sample caused by the impact of a high energy ion from the unfocussed ion source, said sensor means producing a second signal S representing said sample characteristic property; and a correlator means to correlate and store said first signal with said second signal by means of coincidence.

2. The apparatus of claim 1 wherein the high energy ions have an energy of at least approximately 1 MeV.

3. The apparatus of claim 1 wherein the source of ions is from a radioactive alpha particle emitter.

4. The apparatus of claim 1 wherein the source of ions is a particle accelerator.

5. The apparatus of claim 1 wherein the source of ions is from a fission source, said ions being fission fragments.

6. The apparatus of claim 1 wherein the photon projection system is an optical lens system of a conventional optical microscope to project the photon image at high magnification of from approximately 1× to approximately 10000×.

7. The apparatus of claim 6 wherein the optical lens system comprises a defining aperture positioned near the sample, said aperture preventing ions from striking the sample except in the region of the aperture opening.

8. The apparatus of claim 6 wherein the unfocussed source of high energy ions is positioned onto the sample-side of the objective lens of the microscope.

9. The apparatus of claim 6 wherein the optical lens system has a first objective lens proximate to the sample, wherein said unfocussed source of high energy ions is positioned proximate to the first objective lens as an annulus around the outer perimeter of said first objective lens.

10. The apparatus of claim 1 wherein the photon projection system comprises a single lens to project an image of the photons onto the photon position sensitive detector.

11. The apparatus of claim 1 wherein the sample is a condensed matter solid selected from a metal, semiconductor and insulator.

12. The apparatus of claim 1 wherein the sample is a liquid.

13. The apparatus of claim 1 wherein the sample is a specimen of biological origin.

14. The apparatus of claim 1 wherein the sample is a specimen of geological origion.

15. The apparatus of claim 1 wherein the sample is a discreet electronic/photonic component selected from a detector, transistor, diode, and laser.

16. The apparatus of claim 1 wherein the sample is an integrated electronic/photonic circuit selected from a memory, central processing unit, and communications device.

17. The apparatus of claim 1 wherein the photon position sensitive detector comprises a photocathode and multiple microchannel plates to amplify the photon signal.

18. The apparatus of claim 17 wherein the photon position sensitive detector additionally comprises a resistive anode encoder.

19. The apparatus of claim 17 wherein the photon position sensitive detector additionally comprises a charge coupled device.

20. The apparatus of claim 17 wherein the photon position sensitive detector additionally comprises a CMOS image sensor.

21. The apparatus of claim 1 wherein the sensor means measures the current transient of each ion that strikes the sample.

22. The apparatus of claim 21 wherein the sensor means comprises a high frequency amplifier followed by a transient digitizer electronically connected to the sample.

23. The apparatus of claim 21 wherein the sensor means comprises a charge sensitive preamplifier followed by a transient digitizer electronically connected to the sample.

24. The apparatus of claim 21 wherein the sensor means integrates the current transient and provides a signal pulse with pulse height proportional to the total charge collected following the impact of an individual ion.

25. The apparatus of claim 24 wherein the sensor means comprises a charge sensitive electronic preamplifier electronically connected to the sample and followed by a spectroscopic amplifier to produce a pulse whose height is proportional to the collected charge following the impact of an individual ion.

26. The apparatus of claim 1 wherein the sample is a semiconductor digital circuit and wherein the sensor means comprises means to determine the presence of a malfunction of the digital circuit and to provide an associated signal of this malfunction by the generation of a voltage pulse.

27. The apparatus of claim 26 wherein the sensor means is an integrated circuit tester adapted for measurement of broad beam single event effects testing of static and dynamic random access memories and microprocessors.

28. The apparatus of claim 1 wherein the correlator means comprises a multiple analogue-digital-converter based multi-parameter pulse-height analysis system.

29. The apparatus of claim 1 wherein multiple first signals and second signals are correlated to form a list, said list graphically represented as a two dimensional image of the sample characteristic property represented by signal S.

30. A method to correlate, from the interaction of a high energy ion with a sample, a position signal and a signal representing a sample characteristic property, comprising:

directing an unfocussed source of high energy ions at a surface of a sample, wherein photons are emitted in response to impacts from said high energy ions;

projecting said photons onto an image plane of a photon projection system, said photon projection system comprising a photon position sensitive detector placed at the image plane wherein said detector produces a first signal representing the (X,Y) position of said photon;

measuring a characteristic property of said sample, said characteristic property resulting from the impact of the high energy ions at the surface of said sample, wherein said characteristic property is represented by a second signal S; and correlating said first signal with said second signal by means of coincidence.

* * * * *